United States Patent
Nakashima et al.

(10) Patent No.: US 6,409,024 B1
(45) Date of Patent: Jun. 25, 2002

(54) BLOOD PROCESSING DEVICE

(75) Inventors: Hidekazu Nakashima, Yasu-gun; Hiroyuki Sugaya, Otsu; Hiroshi Matsumoto, Otsu; Madoka Kawashima, Otsu; Katsuyoshi Ichikawa, Okazaki; Tsutomu Uesaka, Kyoto, all of (JP)

(73) Assignee: Toray Industries, Inc., Tokyo (JP)

(*) Notice: Subject to any disclaimer, the term of this patent is extended or adjusted under 35 U.S.C. 154(b) by 0 days.

(21) Appl. No.: 09/529,793

(22) PCT Filed: Aug. 27, 1999

(86) PCT No.: PCT/JP99/04649

§ 371 (c)(1),
(2), (4) Date: Apr. 20, 1999

(87) PCT Pub. No.: WO00/12154

PCT Pub. Date: Mar. 9, 2000

(30) Foreign Application Priority Data

Aug. 27, 1998 (JP) .......................... 10-241746
Oct. 21, 1998 (JP) .......................... 10-299438
Oct. 21, 1998 (JP) .......................... 10-299439
Oct. 21, 1998 (JP) .......................... 10-299440

(51) Int. Cl.$^7$ ............................. B01D 63/02
(52) U.S. Cl. ............... 210/456; 210/321.79; 210/321.8; 210/321.88; 210/321.89; 422/44
(58) Field of Search .................. 210/321.79, 321.8, 210/321.88, 321.89, 456; 422/44

(56) References Cited

U.S. PATENT DOCUMENTS 5,238,561 A * 8/1993 Sanda et al. ............. 210/321.8

FOREIGN PATENT DOCUMENTS

| JP | 4-305229 | 10/1992 |
| JP | 6-13843 | 2/1994 |
| JP | 7-184994 | 7/1995 |
| JP | 8-57266 | 3/1996 |
| JP | 9-108338 | 4/1997 |

* cited by examiner

Primary Examiner—John Kim
(74) Attorney, Agent, or Firm—Nixon & Vanderhye P.C.

(57) ABSTRACT

A blood processing apparatus which retains little residual blood is provided by a hollow fiber flux fixed to a housing by a partition, with the end portion opened. A blood port provided with a blood intake is attached to the opened end plane. The angle of the blood intake interior wall of the blood port has an inclination θ of 1.5° or less as to the center axis of the blood port. The distance h of the interior face of the blood port and the flux-holding partition it faces is $0.08 D \leq h \leq 0.13 D$ where Q represents the intersection between a hypothetical line which passes through the end portion P of the inner plane of the blood port and is orthogonal with the partition and a hypothetical extension line from the ceiling plane of the blood port, h represents the distance between the partition and the intersection Q, and D represents the diameter at the end portion of the inner plane of the blood port. The blood processing apparatus is used for blood purifying, dialysis, ultrafiltration, and the like.

7 Claims, 6 Drawing Sheets

BLOOD PROCESSING DEVICE

TECHNICAL FIELD

The present invention relates to a blood processing apparatus suitably used for blood purifying, dialysis, ultrafiltration, and the like.

BACKGROUND ART

Blood processing apparatuses which use hollow fibers as a separating membrane have conventionally been used for purifying blood, and separating specified components within the blood. Such blood processing apparatuses include blood dialysis apparatuses, blood filtering apparatuses, blood plasma separating apparatuses, artificial lungs, and the like.

It is required of these blood processing apparatuses that, along with the functions of blood purifying, separating specified components and the like, there is no coagulation of blood during processing, and that all of the blood is returned into the body of the patient at the time of completing the processing. However, with conventional blood purifiers, there was activation of blood coagulation systems during dialysis, and defective replacement with the saline solution in the blood return operation at the time of ending the processing, resulting in a phenomena called residual blood wherein blood remains within the dialysis apparatus.

DISCLOSURE OF THE INVENTION

It is an object of the present invention to provide a blood processing apparatus with little residual blood.

The object of the present invention is achieved by the following configuration.

(1) A blood processing apparatus has a hollow fiber flux fixed to a housing by a partition with the end portion thereof opened, and a blood port provided with a blood intake attached to the opened end plane; wherein the angle of the blood intake wall provided to the blood port has an inclination $\theta$ of 1.5° or less as to the center axis of the blood port, and the expression $0.08\,D \leq h \leq 0.13\,D$ holds wherein Q represents the intersection between a hypothetical line which passes through the end portion P of the inner plane of the blood port and is orthogonal with the partition and a hypothetical extension line from the ceiling plane of the blood port, h represents the distance between the partition and the intersection Q, and D represents the diameter at the end portion of the inner plane of the blood port.

(2) A blood processing apparatus according to (1), wherein the angle $\beta$ formed between the hypothetical extension line from the ceiling plane of the blood port and the partition is $40° \leq \beta \leq 10°$.

(3) A blood processing apparatus according to (1), wherein $db/da \geq 0.95$ and/or $D-da \leq 2$ mm hold wherein da represents the major axis of the envelope at the opening end portion of the hollow fiber flux and db represents the minor axis thereof.

(4) A blood processing apparatus according to (1), wherein inner plane coarseness of the hollow fiber is 0.5 $\mu$m per 0.1 mm reference length or less.

(5) A blood processing apparatus according to (1), wherein inner plane coarseness of the blood port is 0.3 $\mu$m per 0.1 mm reference length or less.

(6) A blood processing apparatus has a hollow fiber flux fixed to a housing by a partition with the end portion thereof opened, and a blood port provided with a blood intake attached to the opened end plane; wherein inner plane coarseness of the hollow fiber is 0.5 $\mu$m per 0.1 mm reference length or less.

(7) A blood processing apparatus has a hollow fiber flux fixed to a housing by a partition with the end portion thereof opened, and a blood port provided with a blood intake attached to the opened end plane; wherein inner plane coarseness of the blood port is 0.3 $\mu$m per 0.1 mm reference length or less.

(8) A blood processing apparatus according to (1), (6), or (7), wherein the roughness of the blood contacting portion of the partition is 10 $\mu$m per 30 $\mu$m reference length or less.

(9) A blood processing apparatus according to (1), (6), or (7), wherein the ratio of hollow fibers having a minor axis 70% or shorter than the diameter thereof in the event that the cross-section of the hollow fibers is assumed to be a perfect circle is 1% or less of the entire number of hollow fibers built into the blood purifier.

(10) A blood processing apparatus according to (1), (6), or (7), wherein the hollow fibers comprise polymers that have been made to be hydrophilic as a component.

(11) A blood processing apparatus wherein, in the event that a model blood exhibiting the same viscosity properties (viscosity—shear speed relation) as those of human blood at 37° C. is pumped at an amount of 1.3 times the blood filling capacity of the blood processing apparatus and then 125 ml of a phosphoric acid buffer solution per valid unit membrane area of the blood processing apparatus is pumped at 100 ml per minute, the subsequently residual model blood amount within the blood processing apparatus is 1.5 ml per valid unit membrane area or less.

(12) A blood processing apparatus according to (11), wherein a fluid comprising xanthan gum, the phosphoric acid buffer solution, and washed bovine red blood cells, is used as the model blood.

BEST MODE FOR CARRYING OUR THE INVENTION

Figure 1:
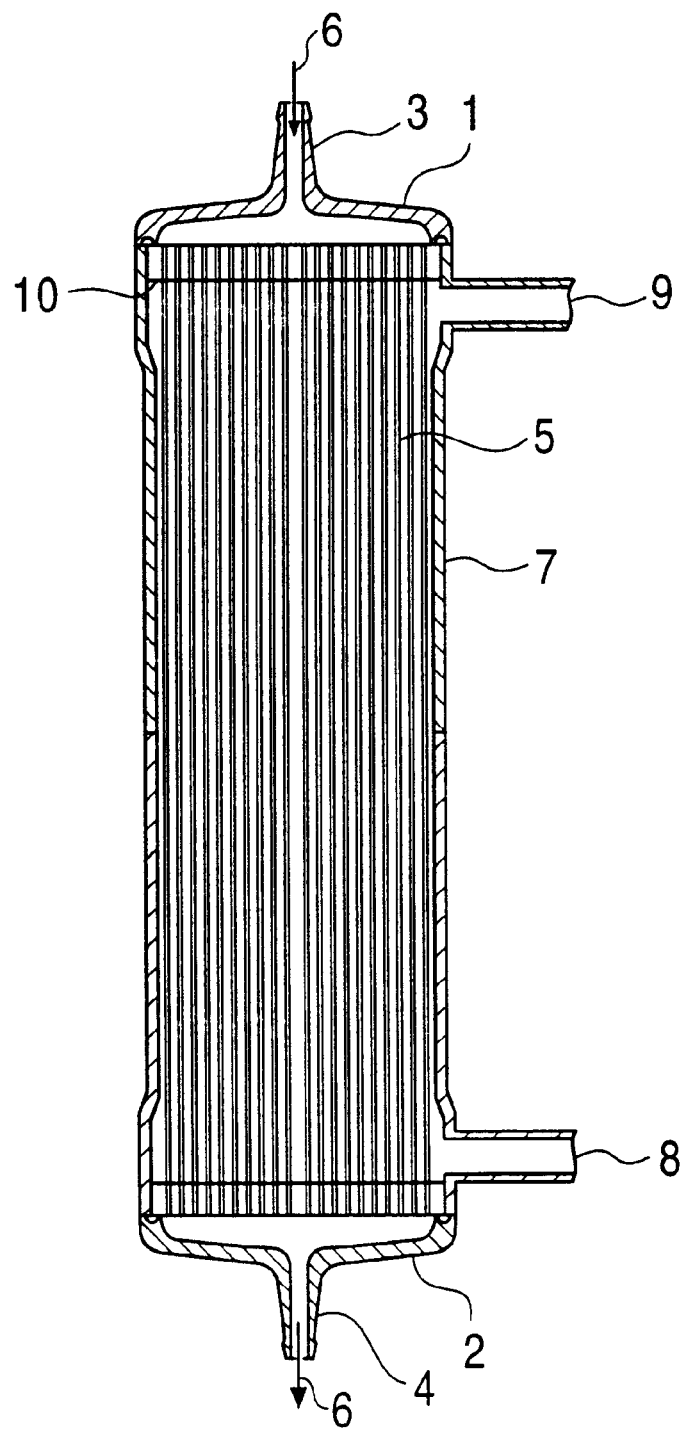
FIG. 1 is a cross-sectional diagram illustrating an example of a blood processing apparatus according to the present invention.
Figure 3:
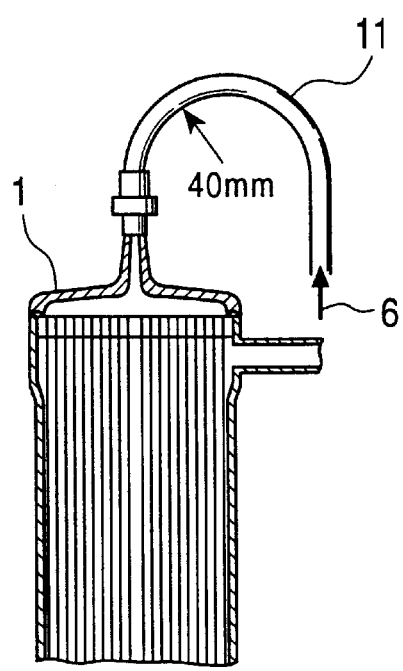
FIG. 3 is a diagram illustrating an example of the connection state of the blood circuit of the present invention.

Though the basic structure of the blood processing apparatus according to the present invention is not particularly restricted, a general arrangement has, for example as shown in FIG. 1, a flux of hollow fiber inserted into a cylindrical plastic case with both end portions of the hollow fiber being sealed off with resin, with intake and outlet ports provided for respective flowing of blood on the inside of the hollow fibers, and dialysis fluid, saline solution, filtering water, etc., on the outside thereof. In FIG. 1, reference numeral 1 is an intake side blood port provided so as to guide blood into the space within the hollow fiber 5 and to partition with the outside. The blood 6 is introduced through a blood intake 3 provided to the intake side blood port. Reference numeral 2 is an outlet side blood port provided in order to collect the blood which has passed through the space inside the hollow fibers, to discharge from the blood output 4, and to isolated from the outside. Reference numeral 7 denotes housing for storing the hollow fiber flux. An intake 8 and outlet 9 for blood processing fluid are provided to the housing. Reference numeral 10 denotes a partition fixed to the housing at the end portion of the hollow fiber flux, so that the inside and outside thereof is liquid-tight, i.e., such that the blood flowing through the space within the hollow fibers does not mix with the blood processing fluid flowing at the outside thereof, and so that the space within the hollow fibers is connected to the space within the blood port, whereby the blood and the blood processing fluid only come into contact via the hollow fibers. As shown in FIG. 3, a blood circuit 11 is connected to the blood intake 3 and the blood outlet 4.

Now, a first method for solving the above problem is to use a blood port with a specific internal plane form. That is, with a blood processing apparatus which has a hollow fiber flux fixed to a housing by a partition with the end portion thereof opened, and a blood port provided with a blood intake attached to the opened end plane, the angle of the blood intake inner wall provided to the blood port has an inclination $\theta$ of 1.5° or less as to the center axis of the blood port, and the expression $0.08\ D \leq h \leq 0.13\ D$ holds wherein Q represents the intersection between a hypothetical line which passes through the end portion P of the inner plane of the blood port and is orthogonal with the partition and a hypothetical extension line from the ceiling plane of the blood port, h represents the distance between the partition and the intersection Q, and D represents the diameter at the end portion of the inner plane of the blood port. By making the angle of the blood intake inner wall provided to the blood port to have an inclination $\theta$ value of 1.5° or less as to the center axis of the blood port, the flow of blood introduced from the blood circuit is rectified at the blood intake portion, so the flow of blood within the blood port is not easily affected by the state in the blood circuit (primarily the bending thereof). Also, it is preferable that the value of $\theta$ be 0.5° or greater. That is because mold separation is easier at the time of forming the blood port form by injection molding. Also, the inclination $\theta$ includes both cases of the flow channel widening in the direction of the blood flow and the flow channel narrowing in the direction of the blood flow, and in either case inclination $\theta$ of 1.50 or less is sufficient.

Also, it is preferable that the distance L that the above inclination $\theta$ is maintained in the axial direction from the blood intake or blood outlet tip is 10 mm or greater, and further preferably 17 mm or greater. Though this distance is preferably long in order to make it difficult for the flow within the blood port to be affected by the bending near the blood intake of the blood circuit, but taking into consideration the possibility that excessive force may be placed on the suddenly-widening portion E of the channel of the blood port in the event that external force is placed near the tip of the blood intake or outlet, and the burden placed on the patient by increasing the capacity of the blood port, this distance is preferably 25 mm or less.

Also, an arrangement wherein $0.08\ D \leq h \leq 0.13\ D$ allows the resistance of blood expanding to the perimeter of the blood port to be reduced so that blood can be caused to flow through all reaches of the blood port in a uniform manner. Further, an arrangement wherein the angle $\beta$ formed between the hypothetical extension line from the ceiling plane of the blood port and the partition is $4° \leq \beta \leq 10°$ does away with excessive space within the blood port, so the introduced blood can be caused to smoothly flow into the hollow fibers, which is desirable.

The fluid motion state of blood normally becomes difficult to observe as the hematocrit of the blood increases, but can be observed relatively easily by using a spot light source such as used with microscopes. The above state of the blood flowing through all reaches of the blood port in a uniform manner can be observed by concentric waves from directly below the blood intake toward the blood port end portion.

Conventionally, it has been thought that the greater the value of the inclination $\theta$ of the blood intake inner wall is as to the center axis of the blood port, the more uniformly blood can be dispersed within the blood port. However, with the present invention, it has been found that a large $\theta$ value causes the flow within the blood port to be easily effected by the state of the blood circuit, causing channeling within the blood port. In the event of using blood processing apparatuses in clinical conditions, generally, the blood port at the blood intake side is at the top. At this time, the blood circuit attached to the blood intake droops downward due to own weight and the weight of the blood. Accordingly, the blood circuit bends downward near the blood intake. In the event that blood passes through the bent blood circuit, turbulence is caused in the flow. Observing the flow at the blood port portion at this time using the above-described spot light source, the flow speed in the bending direction of the blood circuit and the flow speed in a direction having an angle of 180° as to the bending direction are faster than the other flow directions. While the blood flows in these two directions flow into the hollow fibers, a portion thereof collides with the inner wall of the end of the blood port and then changes into a circumference flow direction, and the flow in the opposing circumference direction that has been created collides therewith, resulting in stagnation at that point. The flow speed at the stagnation area is slower than that at other areas, and the blood at this portion is not easily replaced with newly introduced blood, so the blood coagulation system is activated, resulting in increased viscosity of the blood, separating of components in the blood, and in the worst case there is danger of the blood coagulating. Incidentally, the stagnation area can be easily discerned by irradiation of the spot light source, since the color tone differs from that of other portions. In the event that blood dialysis is actually performed in such as state, the opening or interior of the hollow fibers opening near the stagnation area become bottlenecked or plugged due to blood components, resulting in blood processing not being performed efficiently, or causing a phenomena called residual blood wherein not all of the blood within the blood processing apparatus is returned to the patient even though a blood return operation is performed at the time of ending the blood dialysis using a saline solution.

Figure 2:
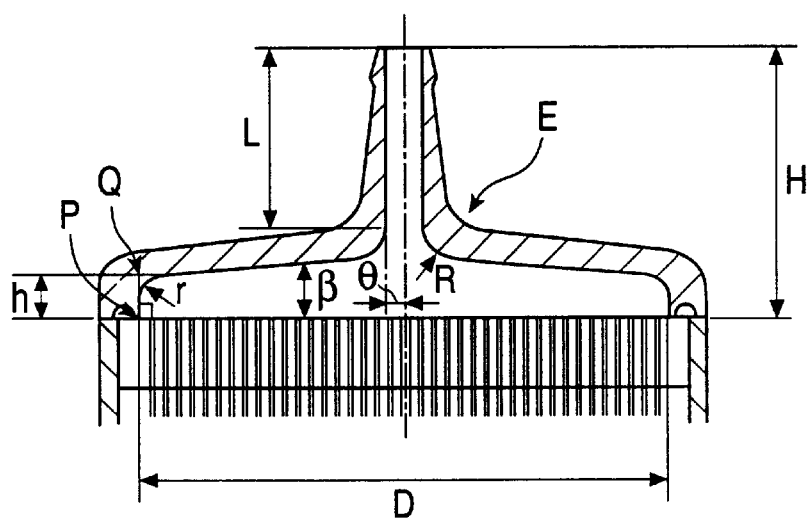
FIG. 2 is a cross-sectional diagram illustrating an example of the blood port portion of the blood processing apparatus according to the present invention.

Now, description will be made regarding the measurement methods for the inclination $\theta$, $\beta$, and distance D and h. In order to correctly measure the inner plane form of the blood port portion, first, the blood port is detached from the blood processing apparatus such there is no deformation thereof. Next, the blood port is cut along a plane passing through the center axis thereof. Preferably, following cutting with a saw or the like along a position shifted from the plane passing through the center axis thereof, the cut plane is polished using sandpaper or the like, so that the plane passing through the center axis is clearly manifested. Following coloring the cross-section plane of the blood port white or a-like procedure such that the cross-section plane can be easily copied, the cross-section plane is copied into paper using a copier which has extremely little warping. In order to measure more correctly, a blown up copy enlarged twice or more in the length of the cross-section is preferable. The angle and length of the portions of interest are measured as shown in FIG. 2 upon the obtained paper. The actual measurement length can be obtained by dividing these by the ratio of enlargement.

In the event that the inner plane form of the blood intake and outlet and the ceiling plane of the blood port do not have a linear portion, the inclination of a tangent line on the inner plane at a point 5 mm in the axial direction from the tip of the blood intake and output toward the partition as to the center axis of the blood port is taken as θ. Also, the angle formed between a tangent line on the blood port ceiling plane at a point 10 mm from the inner plane of the blood port end portion toward the center and the partition is taken as β.

In the present invention, with da representing the major axis of the envelope at the opening end portion of the hollow fiber flux and db representing the minor axis thereof, it is preferable that db/da≧0.95 and/or D−da≦2 mm hold. In the event that the degree of effects of bending of the blood circuit are pronounced, the blood flow cannot be completely rectified event in the event that the value of θ is made to be 1.5° or smaller, resulting in stagnation within the blood port as described above, but arranging so that db/da≧0.95 and/or D−da≦2 mm hold facilitates ease of blood at the stagnation area near the inner wall at the end portion of the blood port to flow into the hollow fibers, thereby reducing the amount of stagnation.

Figure 4:
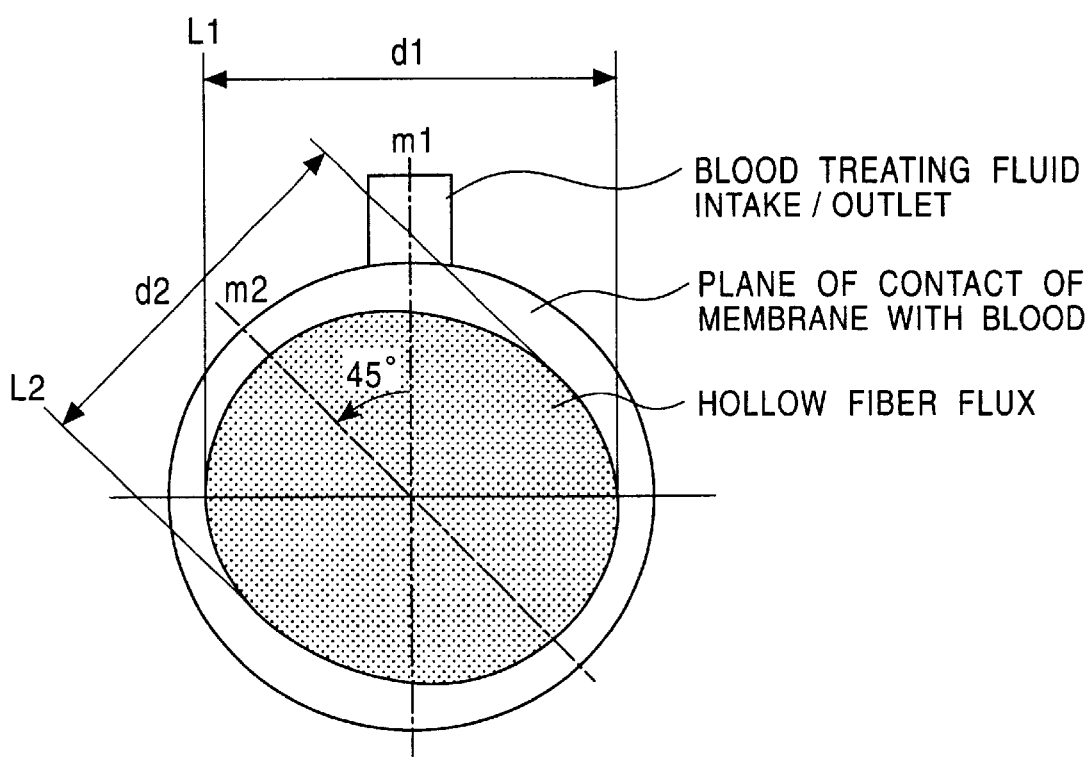
FIG. 4 is a diagram illustrating the method for measuring da and db in the blood processing apparatus according to the present invention.

Now, the major axis da and minor axis db of the envelope at the opening end portion of the hollow fiber flux are measured as follows. First, the blood port of the blood processing apparatus is removed, and as shown in FIG. 4, a straight line m1 equally dividing the blood processing fluid intake or outlet and the plane of contact with blood of the partition is drawn. A pair of parallel lines L1 parallel with m1 are positioned on either side of the hollow fiber flux at the hollow fiber opening plane, with the distance between the two lines as d1. In rare occasions, one to several hollow fibers may be protruding in the direction out of the case, but these are viewed as part of the hollow fiber flux as well. Next, m1 is rotated 45° as to the center of the blood contact plane of the partition, and this line is taken as m2. A pair of parallel lines L2 parallel with m2 are positioned on either side of the hollow fiber flux, with the distance between the two lines as d2. Subsequently, rotation is made in the same manner at 45° at a time, thereby measuring d3 through d8, thus obtaining the distance values of all eight positions. The greatest value of d1 through d8 is taken as da, and the smallest value thereof is taken as db.

A second method for solving the above problem is to keep the inner plane coarseness of the hollow fibers to or below a specified value. That is, the inner plane coarseness of the hollow fibers is made to be 0.5 μm or less in the event that the reference length is 0.1 mm.

The inner plane coarseness of the hollow fibers as defined here is obtained by extracting a reference length 0.1 mm of the hollow fiber cross-section curve obtained by planes passing through the axis of the hollow fiber and the inner surface of the hollow fiber, and representing the gap, obtained by placing two lines parallel to the average line (a line set such that the squared deviation from the average line to the cross-section curve is minimal) thereof on either side of the cross-section curve of the hollow fiber, in increments of μm. This inner. plane coarseness can be measured with a scanning white-light interferometric microscope. With the present invention, ten hollow fibers are arbitrarily selected from the flux made up of multiple hollow fibers, each is measured at one arbitrary position therein, and the average value of the inner surface coarseness is 0.5 μm or less. In the event that roughness exceeding this exists in a distance of 0.1 mm, the blood platelets are stimulated by blood flow, which tends to cause residual blood. It is preferable that the inner surface coarseness is 0.3 μm per 0.1 mm reference length or less, and more preferably 0.1 μm or less.

Also, combining the second method with the above first method is even more preferable.

A third method for solving the above problem is to keep the inner surface coarseness of the blood port to or below a specified value. That is, the inner surface coarseness of the blood port is made to be 0.3 μm or less in the event that the reference length is 0.1 mm. The inner surface coarseness as defined here is the same as described above, and is obtained by extracting a reference length 0.1 mm of the cross-section curve of the inner surface of the blood port, and representing the gap obtained by placing two lines parallel to the average line thereof on either side of the cross-section curve of the inner surface of the blood port in increments of μm. This inner surface coarseness was measured at five arbitrary position on the inner plane of the blood port coming in contact with blood, using a confocal microscope manufactured by KEYENCE CORPORATION (measuring unit VF-7510, controller VF-7500).

Also, combining the third method with the above first method is even more preferable.

With the present invention, it is preferable that the roughness of the blood contacting portion (end plane) of the partition be 10 μm per 30 μm reference length or less. The plane roughness as defined here is the same as described above, and is obtained by extracting a reference length 30 mm of the cross-section curve of the partition, and representing the gap obtained by placing two lines parallel to the average line thereof on either side of the cross-section curve of the partition in increments of μm. The surface roughness of the partition is an average value of three points each for near the perimeter of the hollow fiber flux at the three-o'clock direction with the dialysis fluid side nozzle at the twelve-o'clock direction, the center portion, the resin portion at the perimeter of the hollow fiber flux at the nine-o'clock direction, and the hollow fiber portion, in the measurement of the resin portion and the hollow fiber portion. The roughness value of the blood contact portion was measured using a surface form measuring microscope manufactured by KEYENCE CORPORATION. With the present invention, the surface roughness of the blood inflow portion was measured by measuring the resin portion and the hollow fiber portion at 2500 times magnification with the surface form measuring microscope manufactured by KEYENCE CORPORATION (VF-7500, VF7510 system).

In the case of hollow fiber blood processing apparatuses, the partition is normally formed by cutting the hollow fiber seating portion with a cutter, but roughness is generated at the resin portion, between the resin and the hollow fibers, and at the hollow fibers, at the time of cutting or in subsequent storing. Existence of such roughness may activate blood platelets, or the blood flow may become turbulent and thereby activate blood platelets, and the activated blood platelets may adhere to the hollow fibers and become residual blood. In order to prevent such a phenomena from occurring, it is preferable that the average roughness at the resin portion, between the resin and the hollow fibers, and at the hollow fibers, be 10 μm or less, more preferably 5 μm or less, and even more preferably 3 μm or less. Also, in the event that there are dimples in the resin portion, there may be cases wherein blood collects in the dimples, and blood activation occurs. Accordingly, it is preferable that the average roughness of the resin portion between hollow fibers also be 10 μm or less, more preferably 5 μm or less, and even more preferably 3 μm or less. This roughness is an average value obtained from eight measurement points, by finding places wherein the distance between hollow fiber and hollow-fiber is 150 to 250 μm, and measuring in the parallel and perpendicular directions to the cross-sectional direction thereof at the three-o'clock direction, center portion, nine-o'clock direction, and twelve-o'clock direction portions. With the present invention, between the resin and hollow fibers was measured at 1250 times magnification with the surface form measuring microscope manufactured by KEYENCE CORPORATION. In order to reduce the roughness, increasing the hardness of the sealing resin at the time of cutting, increasing the hardness of the cutting blade, lowering the speed for cutting, making the cutting thickness at the time of cutting thinner are effective methods, and for example, since low harness in sealing resin results in greater surface coarseness at the resin portion, it is preferable that the Shore A hardness at the time of cutting be 80 or more, and preferable 90 or more. However, in the event that the hardness is too great, the blade is easily damaged and the lifetime thereof is reduced, so this is preferably 98 or lower from a practical perspective. Also, since burrs occur at the cross-section plane of the hollow fibers in the event that the blade tip angle of the cutting blade is too great, the blade tip angle is preferably 50° or smaller, more preferably 40° or smaller, and even more preferably 30° or smaller.

With the present embodiment, in the event that the cross-section of the hollow fibers is assumed to be a perfect circle, the ratio of hollow fibers having a minor axis 70% or shorter than the diameter thereof is preferably 1% or less of the entire number of hollow fibers built into the blood purifier. In the event that there is flattening in part of the hollow fibers making up the hollow fiber flux and fluid motion is poor therein, blood, saline solution, and the like prefer to flow through other normal hollow fibers. Consequently, hollow fibers with poor fluid motion are particularly prone to occurrence of residual blood.

Further, at the opening end plane, the greater the ratio of the area of open hollow fiber holes in the blood port inner area is, the more the blood flow rate improves at the end plane, thereby increasing fluid motion. The hole ratio is preferably 28% or higher, and more preferably 30% or higher.

With the present invention, it is preferred that the hollow fibers comprise polymers that have been made to be hydrophilic as a component.

In the present invention, a polymer membrane that has been made to be hydrophilic refers to a polymer membrane of hydrophobic polymers that have been made to be hydrophilic by one method or another, as the membrane material. This includes, but is not particularly restricted to, copolymerization of hydrophilic monomers and hydrophobic monomers, blending hydrophilic polymers and hydrophobic polymers to form a membrane, causing junction or adhesion of hydrophilic polymers to the surface of a membrane made up of hydrophobic polymers, chemical processing or plasma processing of the surface of a membrane made up of hydrophobic polymers, and so forth, so long as the material is made to by hydrophilic. As for hydrophilic components used for the polymers that have been made to be hydrophilic, polyalkylene oxides such as polyethylene glycol, polyvinyl pyrolidone, polyvinyl alcohol, polyhydroxyethyl methacrylate, and like hydrophilic polymers are preferable since these are greatly effective in suppressing adhesion of blood platelets. Examples that can be given for the hydrophobic components include ester methacrylate, ester acrylate, ethylene, propylene and other olefins, acrylonitrile, methacrylonitrile and other polymers formed of addition polymerization compounds having carbon-carbon double bonds thusly, polysulfone, cellulose, and like polymers, and so forth can be given as examples, but are not restricted in particular as long as the components can be used as membrane material.

Examples of membranes formed of polymers that have been made to be hydrophilic include hollow fiber formed of polyethylene oxide copolymers such as polyethylene oxide-polyacrylonitrile copolymers, polyethylene oxide-polymethyl polymethacrylate copolymers, etc., polyvinyl pyrolidone-polysulfone blend membranes, polyvinyl pyrolidone-polyamide blend membranes, polyvinyl alcohol-polyethylene copolymer membranes, polyethylene glycol graft cellulose membranes, etc. Of these, hollow fibers formed of polyethylene oxide copolymers are preferable, since anti-clotting can be improved, and manufacturing is easy.

Making membrane hydrophilic is a process that is preferable for suppressing adhesion of blood components such as blood platelets, and it is preferable that this is a so-called anti-clotting membrane which suppresses adhesion of blood platelets. This anti-clotting nature can be confirmed by observing the membrane surface with an electron microscope following contact with blood. Although the degree of hydrophilic processing is not particularly specified, it is preferable that the amount of adhesion of blood platelets be reduced by 10% or more as compared to a simple hydrophobic membrane state. It is further preferred that this be reduced by 20% or more. Though using such hydrophilic membrane reduces the effects of protein adhesion as compared to such which has not been made to be hydrophilic, residual blood can be greatly reduced.

This degree of hydrophilic processing depends on the type of membrane even in the event that the hydrophilic component amounts are the same, but comparison between membrane types can be evaluated by the following method with polymethyl methacrylate as a reference.

Hollow fibers are cut into a length of approximately 22 cm, 30 of these are bundled and placed in a polystyrene tube provided with a dialysis fluid intake and outlet port, both ends are fixed with resin, both ends are cut following hardening of the resin, and the blood port is attached above a funnel, thereby forming a blood processing module for evaluation. Rabbit platelet rich plasma (hereafter referred to as "PRP") is caused to flow over this module porous membrane at a temperature of 37° C. and at blood linear velocity of 1 cm/s for 20 minutes. Following cleansing with saline solution, this is fixed with a glutaraldehyde saline solution. Following cleansing with pure water one day later, this is freeze-dried. This sample is subjected to platinum-palladium vapor deposition, and the platelets adhered to the membrane surface are observed using a scanning electron microscope. Now, the PRP here is obtained by drawing blood from the carotid artery using a syringe containing a 3.8% solution of sodium citrate filled to $\frac{1}{10}$ of capacity, which is subjected to silicon treatment and immediately transferred to a test tube, and subjected to centrifugal sedimentation at 800 to 1000 rpm for 8 to 15 minutes. The number of platelets is adjusted so as to be 200,000/µl or more. Evaluating a polymethyl methacrylate membrane (BK-P membrane manufactured by TORAY INDUSTRIES) with the above method, there is adhesion of $5 \times 10^{-6}$ pieces/cm$^2$. The degree of anti-clotting nature of the membrane according to the present invention is preferably $10^{-6}$ pieces/cm$^2$ or lower in this platelet adhesion evaluation, and is more preferably $5 \times 10^{-5}$ pieces/cm$^2$ or lower in amount of adhesion. Further, membrane with adhesion amount of $5 \times 10^{-2}$ pieces/cm$^2$ or lower exhibits extremely little adhesion of platelets, so deterioration of the membrane and blood clogging called residual blood can be reduced substantially, and thus is particularly preferable.

The hollow fibers are formed by dissolving copolymers in a solvent and forming membrane. The hollow fibers are obtained by using multiplex slits capable of causing flowing of liquid or air for forming the hollow portion on the inside and a spinning fluid wherein polymers are dissolved in a solvent on the outside, and discharging these fluids and gasses to a coagulation bath. Examples of fluid injected on the inside include the solvent of the spinning fluid, coagulating agents such as water or alcohol, mixtures thereof, or the copolymers or non-solvent hydrophobic liquids mixed with the copolymers, e.g., n-octane, aliphatic hydrocarbons such as liquid paraffin, fatty acid esters such as isopropyl myristate, and so forth. In the event that a hydrophilic coagulant is used, hydrophilic polymer components with high affinity to the coagulant migrate to the inner surface of the membrane, and coagulate. Also, in the event that the discharged fibers gel in mid-air due to temperature change, or rapidly form sturdy structures due to coagulation, inert gasses such as nitrogen gas or air can be used by self-suction or pressuring. Such gas injection methods are extremely advantageous methods from the perspective of process as well. In the event that the fluid is such wherein gelling is caused by temperature change, the gelling can be promoted by blowing cold air on the dry portion. Generally, the membrane thickness of the hollow fibers is controlled by the amount of discharge of the spinning fluid, and he inner diameter by the amount of injected liquid or air.

The coagulation bath is usually made up of a coagulating agent such as water or alcohol or mixtures thereof with the solvent comprising the spinning fluid. The components of the coagulating bath greatly affect the spinning stability and membrane structure within the hollow fibers, by the coagulating properties thereof.

In order to reduce the roughness on the inner surface of the hollow fiber, the molecular weight of the polymers used is preferably small, and the viscosity of the dissolved solution low. The optimal viscosity is selected as appropriate according to the polymers used, the solvent, and the membrane-forming conditions. In the event that polymethyl methacrylate is used as the polymer, dimethyl sulfoxide as the solvent, and membrane formation performed in injecting air within the hollow fibers, the viscosity at 110° C. is preferably 2000 poise or lower, more preferably 1200 poise or lower, and even more preferably 500 poise or lower. In the event that polysulfone is used, and a coagulating liquid is injected inside to form the hollow fibers, the inner surface is formed in is a short time so , is order to smooth the inner surface, the diameter of the hollow fiber is further preferably made the same as the diameter of the multiplex slit from which the polymer is discharged, and a great amount of liquid with high coagulating properties such as water added to the inside.

Though means for forming a blood processing apparatus using the obtained hollow fibers is not particularly restricted, an example is as follows. First, the hollow fibers are cut to a necessary length, a necessary number thereof are bundled, and then placed in a plastic case which is the cylinder portion of the blood processing module. Subsequently, temporary caps are placed on both ends thereof, and resin is put in both hollow fiber end portions. At this time, a method wherein the module is rotated with a centrifugal device while resin is put in from the caps or dialysis liquid port is preferable, since the resin is filled in uniformly. Following hardening of the resin, both ends are cut, the portions where the hollow fibers are plugged off with resin are cut away with a cutter, and a blood intake and outlet port called a header is attached, thereby obtaining a blood processing module.

With the present invention, the amount of protein adhering to the hollow fiber surface is preferably 0.1 g/m$^2$ or more but less than 10 g/m$^2$.

The expression that the amount of protein adhering to the hollow fiber surface is 0.1 g/m$^2$ or more means the amount of protein capable of adhering at the time that serum is brought into contact with the membrane. This amount of adhesion can be evaluated by the following method. The blood processing apparatus is erected and held with a clamp, and a circuit is connected to the area through which blood normally flowing the through the inside of the hollow fibers of the blood processing apparatus is caused to flow (hereafter referred to as "blood side") and the area at the outer side the hollow fibers where the where the dialysis fluid side is normally caused to flow (hereafter referred to as "dialysis fluid side"), thus forming a circuit with a blood pump connected to the blood intake side (upper side) and the dialysis fluid outlet side (upper side). The blood processing apparatus is cleansed using 1 liter of saline solution, and is filled with saline solution. An amount of 500 ml of bovine serum is prepared, which is caused to flow at the blood side for 1 minute at 100 ml/min, and the saline solution in the circuit at the blood side is discarded. The remaining bovine serum is placed in a beaker maintained at a temperature of 37° C., perfusion is performed at the blood side for 50 minutes at 200 ml/min, and the lower side nozzle is capped at the dialysis fluid side and filtered at 10 ml/min. An amount of 2 liters of saline solution is used cleanse the blood side for 5 minutes at 200 ml/min, the blood side outlet is connected to the dialysis side intake and cleansed for 10 minutes at 100 ml/min. The blood dialysis apparatus is disassembled, the hollow fibers extracted, and then the membrane is subjected to hydrolysis with 6N hydrochloric acid (135° C., 3 hours) to quantify amino acids, thus calculating the amount of protein. In order to remove protein such as cannot be normally handled by dialysis, and expect inhibiting progression of disease or improvement, adhesion of 0.1 g/m$^2$ of protein or more is preferable, 0.2 g/m$^2$ or more is more preferable, 0.5 g/m$^2$ or more is even more preferable, and preferably 1 g/m$^2$ or more is desirable. However, in the event that adhesion exceeds 10 g/m$^2$, the amount of protein lost at one treatment session is too great, and there is danger of hypoproteinemia.

The fourth method for solving the above problem is to use a blood processing apparatus which has residual blood less than a certain amount with the following evaluation. That is, a model blood exhibiting the same viscosity properties (viscosity—shear speed relation) as those of human blood at 37° C. is pumped at an amount of 1.3 times the blood filling capacity of the blood processing apparatus and then 125 ml of a phosphoric acid buffer solution per valid unit membrane area of the blood processing apparatus is pumped at 100 ml per minute, and the subsequently residual model blood amount within the blood processing apparatus is 1.5 ml per valid unit membrane area or less.

Figure 5:
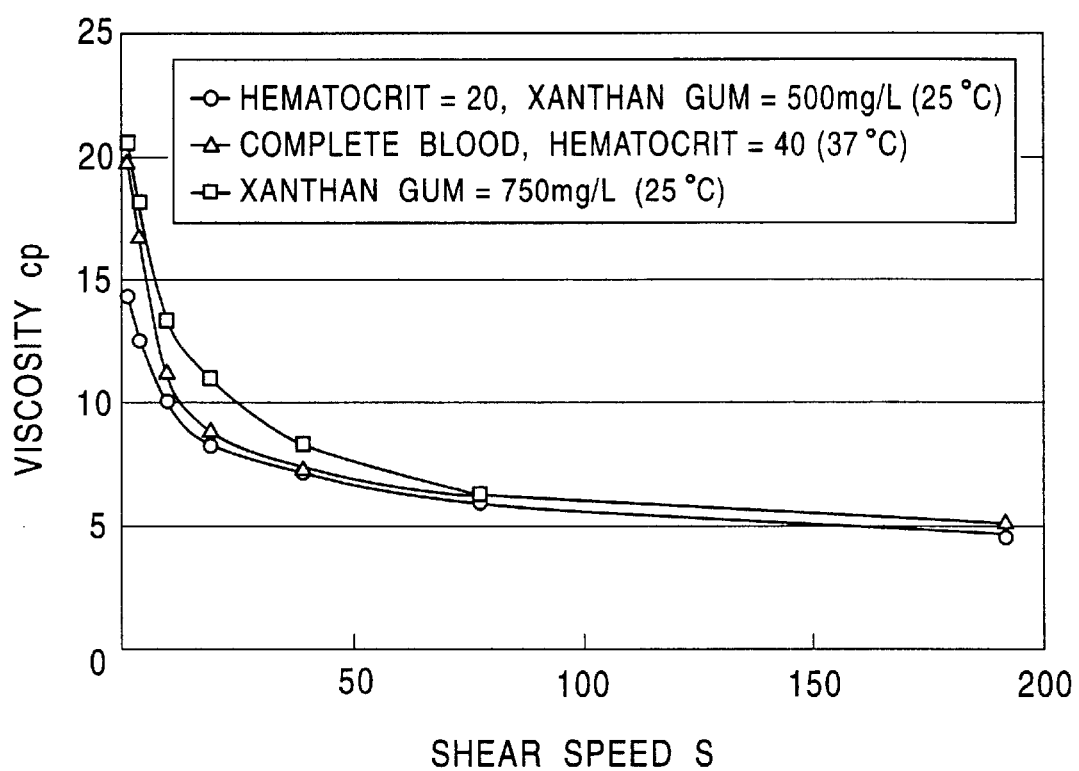
FIG. 5 is a diagram illustrating the viscosity properties in the model blood used in the present invention.

The human blood in the present invention is blood indicating average blood of a healthy person, e.g., with hematocrit (red blood cell volume ratio) of 40% and protein amount in plasma of around 8 g/dL. The measurement values of the viscosity properties (viscosity—shear speed relation) of this blood are shown in FIG. 5. Measurements were made using an E-type viscometer manufactured by TOKIMEC INC. The shear speed was adjusted by the rotating speed of the conical rotor thereof. Now, a fluid which exhibits the same behavior as complete human blood at 37° C. for the relation between viscosity and shear speed has as this relationship viscosity of 10 to 14 cP at a shear speed of 9.6 $s^{-1}$, viscosity of 5 to 7 cP at a shear speed of 76.8 $s^{-1}$, and viscosity of 3 to 6 cP at a shear speed of 192 $s^{-1}$.

A fluid comprising xanthan gum, a phosphoric acid buffer solution, and washed bovine red blood cells, can be used as the model blood. The measurement values of the viscosity properties (viscosity—shear speed relation) of this model blood are shown in FIG. 5. A necessary amount of the phosphoric acid buffer solution was prepared by dissolving. 5.33 mmol of sodium dihydrogenphosphate dodecahydrate, 1.34 mmol of potassium dihydrogenphosphate, and 154 mmol of sodium chloride, dissolved in RO water to make 1 liter.

In the case of a model blood containing red blood cells, the residual model blood amount is measured as follows. First, the blood intake side and outlet side blood ports are removed from the blood processing apparatus, and the fluid remaining in the ports is collected. Next, both blood ports are attached, and xanthan gum/phosphoric acid buffer solution is caused to flow in to the intake side from the blood outlet side, and the inside of the blood processing apparatus is cleansed until no more flowing out of red blood cells from the hollow fibers is observed. Following measuring the liquid remaining inside the blood port and the liquid amount of the above cleansing fluid, 3 ml of each is taken, 3 ml of RO water is added to cause hemolysis of the red blood cells, and the hemoglobin concentration in each liquid is measured from the absorbance thereof of a 414 nm wavelength. The amount of liquid for each is multiplied thereto, thereby calculating the amount of hemoglobin within the blood processing apparatus. Further, the hemoglobin concentration of the model blood is converted into model blood amount, and this is taken as the amount of residual model blood within the blood processing apparatus.

According to these evaluations, the residual blood properties of the blood processing apparatus can be evaluated with a system unaffected by the blood coagulating system, so with blood processing apparatuses with 1.5 ml or less in the residual model blood amount, a blood processing apparatus with markedly reduced residual blood in clinical practice can be provided as compared to blood processing apparatuses with more than 1.5 ml in residual model blood amount.

The effects of the blood processing apparatus according to the present invention regarding residual blood can be confirmed clinically in animal experiments and in dialysis treatment. The ease of activation of blood differs by person or subject, and it is difficult to quantitatively grasp the effects thereof, but in the case of humans, dialysis facilities and dialysis patients can be decided upon to perform evaluation in numbers of ten or more and make judgements thereof based on the same standards, and in the case of animal experiments, samples to be compared can be subjected to parallel perfusion to confirm the effects. The following is an evaluation method with animal experiments. A beagle dog is used as the animal, the hematocrit thereof is adjusted to 33%, blood is extracted from an artery, and perfusion is performed at the inner side of the hollow fibers for 2 hours at 100 ml/min. Extracting blood from two places allows two evaluations to be performed simultaneously, thereby doing away with the effects of difference in subject. After the perfusion, a saline solution is caused to flow for 1 minute at 100 ml/min, following which residual blood is washed out with air, and having performed this operation, the number of fibers which have half or more of the length thereof remaining as externally viewed by the naked eye are counted out of the hollow fibers, thereby judging the residual blood state.

This will be described in further detail in the following embodiments, but the present embodiment is not restricted to these embodiments.

FIRST EMBODIMENT

An amount of 31.7 parts by weight of syndiotactic polymethyl methacrylate (syn-PMMA) having average molecular weight of 400,000 by weight average according to polystyrene conversion GPC method, 31.7 parts by weight of syn-PMMA having average molecular weight of 1,400,000 by weight average, 16.7 parts by weight of isotactic polymethyl methacrylate (iso-PMMA) having average molecular weight of 500,000 by weight average, and 20 parts by weight of polymethyl methacrylate (Co-PMMA) having molecular weight of 300,000 by weight average containing 0.3 mol % of p-sodium sulfonyl styrene were mixed with 376 parts by weight of dimethyl sulfoxide, and stirred for 8 hours at 10° C., thereby obtaining a spinning fluid. The viscosity of the obtained spinning fluid at 110° C. was 1,000 poise.

The obtained spinning fluid was discharged from a ring slit type hollow nozzle with an outer diameter/inner diameter of 2.1/1.95 mm diameter that was maintained at 99° C., at a rate of 1.1 g/min, into the atmosphere. At the same time, nitrogen gas was injected into the hollow interior. The length of the dry portion was 60 cm, and water of 40° C. was used for the coagulation bath. Following washing the coagulated hollow fibers with water, these were subjected to a 5% relaxation thermal processing in at 73% glycerin solution at 75° C., and sampled. The inner diameter/membrane thickness of the hollow fiber was 200/30 µm.

The surface coarseness per 0.1 mm reference length of ten of the obtained hollow fibers was measured under conditions of twice system magnification, using a 20 times magnification object lens with a scanning white-light interferometric microscope (NewView 100) manufactured by ZYGO. The results showed that the average value thereof was 0.08 µm. The hollow fibers were cut into 22 cm length, 15,768 of such fibers were bundled, placed in housing formed of a polystyrene tube with a 35 mm inner diameter having a intake opening and outlet opening for blood processing fluid, both ends thereof were fixed with resin, then cut with a steel blade at a tip angle of 30°, thus forming a smooth plane. The surface coarseness of the blood intake portion (maximum height) at this time was 4 µm, according to measurements made using a surface form measuring microscope manufactured by KEYENCE CORPORATION (VF-7500, VF-7510 system) with a VF-L250 lens. Also, the roughness between hollow fiber—hollow fiber was 5 µm. The minor axis/major axis ratio, db/da, of the fiber flux, was 0.95.

FIG. 2 is a cross sectional diagram of a blood port portion of a blood processing apparatus which is one embodiment of the present invention.

In FIG. 2, θ represents the inclination to the center axis of the blood port, L the length maintained from the tip of the blood outlet in the axis direction, and β an acute angle formed with a hypothetical inclined line passing through the axial line of the blood passing portion. Blood ports were manufactured wherein θ was 1.00, β was 6°, and wherein R, r, H, h, and D were respectively 3 mm, 4 mm, 26 mm, 4 mm, and 43.5 mm, and attached to the blood intake side and outlet side of the blood processing apparatus main unit housing filled with the hollow fibers, thus forming a blood processing apparatus with a valid membrane length of 19 cm, and valid membrane area of 1.6 m². The inner surface coarseness per 0.1 mm reference length for this blood port was 0.3 μm, and D–da was 0.5 mm. Also, permeability thereof was 80 ml/hr·mmHg.

Regarding this blood processing apparatus, evaluation of the fluid motion state within the blood port was performed using bovine blood.

In order to bring the viscosity properties (viscosity—shear speed relation) at 37° C. of the prepared bovine blood closer to the viscosity properties at 37° C. of that of an average dialysis patient (hematocrit 27.5%, total protein volume in plasma of 7 g/dl), dilution was performed using saline solution and bovine plasma, so that the hematocrit was 20.0% and the total protein amount within the plasma was 7 g/dl. Also, 2.5 mmol/L of ethylenediaminetetraacetic acid di sodium was added in order to deactivate the blood coagulation system. Also, as shown in FIG. 3, the blood circuit was bent to 180° at radius of 40 mm and then connected to the blood port. The intake 8 and outlet 9 for the blood processing fluid were both closed with rubber caps.

The above prepared bovine blood heated to 37° C. was used for perfusion in the above blood processing apparatus, and observing the blood fluid motion state macroscopically while applying light to the blood port portion 15 minutes later allowed confirmation of the blood spreading to the perimeter there in a concentric manner in accordance with the pulsing of the blood pump. Also, no stagnation area was observed.

This blood processing apparatus was used for blood dialysis for four hours, and even though the blood circuit was bent near the blood intake opening, there was no non-uniform flow within the blood port or resulting stagnation at any time during the four hour treatment period, blood return was performed smoothly at the time of ending blood dialysis, and there was hardly any residual blood observed.

Four hour blood dialysis was performed on 11 patients 3 times each for a total of 33 times, and the residual blood state following the blood returning operation was observed. The number of hollow fibers with residual blood at the blood processing apparatus side was counted macroscopically, and the degree of residual blood was scored based on Table 1. The resulting average residual blood score was 1.4.

TABLE 1

| Number of hollow fibers with residual blood at blood processing apparatus side | Residual blood score |
| --- | --- |
| None | 0 |
| 1 to 10 | 1 |
| 10 to 30 | 2 |
| 30 to ⅓ of total number | 3 |
| ⅓ to ½ of total number | 4 |
| ½ of total number to all | 5 |

This blood processing apparatus was subjected to a parallel perfusion test using a beagle dog with a dialysis device manufactured by TORAY INDUSTRIES (product name: Filterizer BG-1.6U, hereafter abbreviated as BG1.6U) as a comparative sample. The test was performed four times, the number of hollow fibers with residual blood on the blood processing apparatus side following the blood return operation was counted macroscopically, and the degree of residual blood was scored based on Table 1. The resulting average residual blood score was 1.25, as compared to 3.5 for the BG-1.6.

The amount of residual model blood was measured using the following method.

First, two types of fluid having the same fluid properties as that of complete human blood at 37° C. (ht 40%, Tp 8) were prepared. One as 0.75 g/L of xanthan gum/phosphoric acid buffer solution, and this exhibits at 25° C. or lower the same fluid properties as that of complete human blood at 37° C. The other was washed red blood cells of hematocrit 20%, xanthan gum, 500 mg/L, plus xanthan gum/phosphoric acid buffer solution, and this also exhibits at 25° C. or lower the same fluid properties as that of complete human blood at 37° C. Here, the former shall be referred to as a model polymer fluid, and the later as a model blood. As for the washed red blood cells used here, bovine blood was subjected to centrifugal separation, washed several times with a phosphoric acid buffer solution, and used. The relation between the shear speed of each fluid and the viscosity thereof is as shown in FIG. 5. As shown in FIG. 5, there was viscosity of 10 to 14 cP at a shear speed of 9.6 s$^{-1}$, viscosity of 5 to 7 cP at a shear speed of 76.8 s$^{-1}$, and viscosity of 3 to 6 cP at a shear speed of 192 s$^{-1}$.

Figure 6:
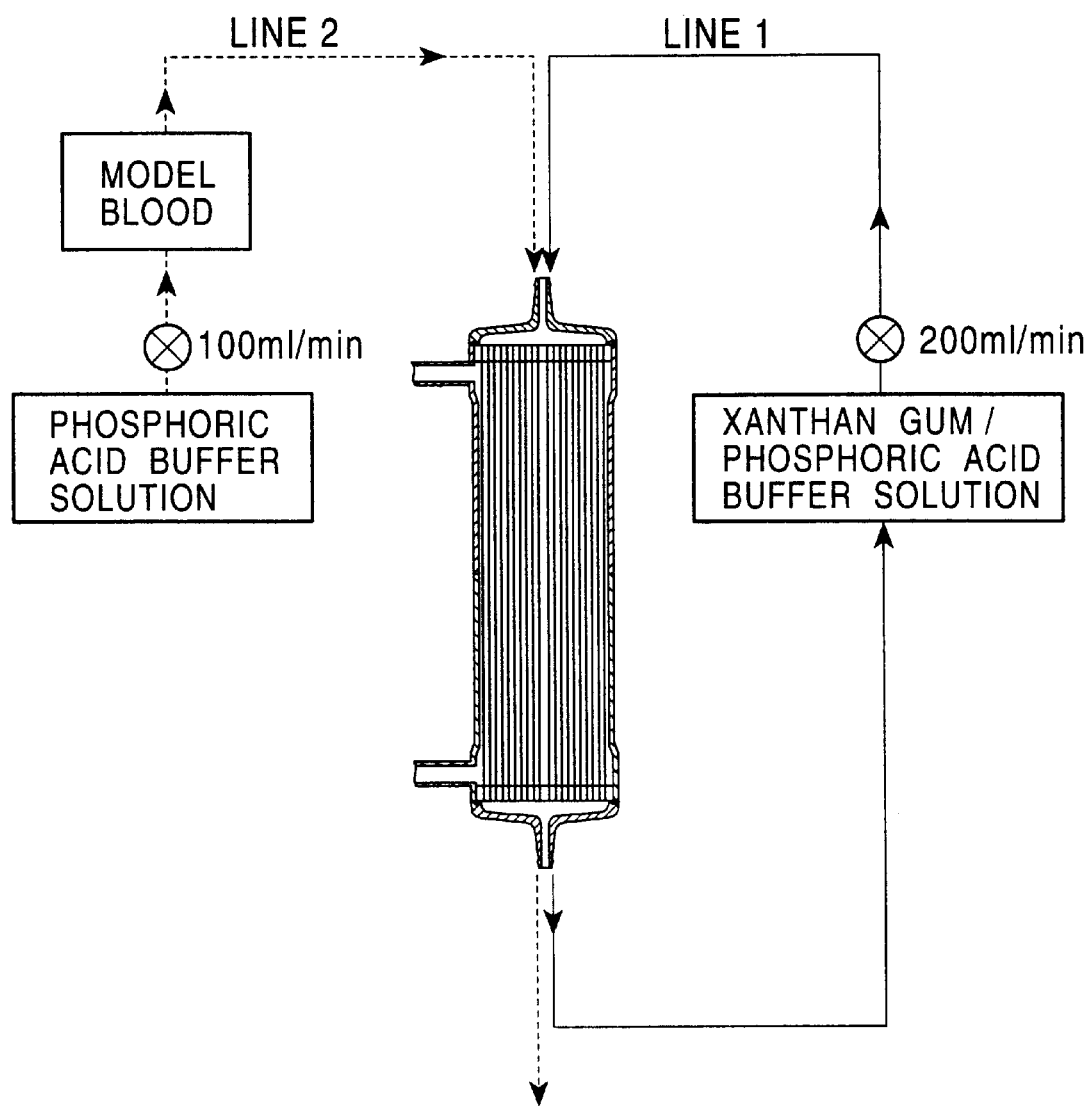
FIG. 6 is a diagram illustrating the equipment used in the model experiment system of the present invention.

In order to observe the flow of blood at the time of flowing into the blood purifying apparatus and at the time of blood return, a device such as shown in FIG. 6 was made, and the blood returning capabilities of the blood purifying apparatus were studied from the amount of residual blood following blood return. All experiments were conducted at 25° C. or lower.

The main operating procedures are as follows.

(1) The model polymer solution heated to 25° C. was circulated through Line 1 for 20 minutes, until the temperature within the blood purifying apparatus was stabilized at 25° C. This was performed in order to stabilizing the temperature environment at a constant 25° C., since viscosity properties are easily affected by temperature.

(2) The circulation of the model polymer fluid was stopped, the circuit was switched to Line 2, and with the state of the circuit being filled with the model blood, connection was made to the blood intake side blood port. This was performed to quantify the residual blood amount following blood return by introducing the model blood containing red blood cells. Switching the circuit allows the amount of red blood cells used to be kept to a small amount.

(3) The model blood was pumped at an amount of 1.28 times the capacity of the blood channel of the hollow fiber type blood purifying apparatus, at a flow speed of 100 ml/min. Following approximately 1.28 minutes, phosphoric acid buffer solution heated to 25° C. flowed into the module, and blood return was begun. The pumping was stopped at the point that 200 ml of blood return had been performed. In clinical practice, the primarily used technique is to perform blood return using 200 ml of saline solution at a flow speed of 100 ml/min, so with the present system the flow speed was set at 100 ml/min, and 200 ml of phosphoric acid buffer solution was used for blood return.

According to the above operations, the fluid motion of the blood at the perimeter of the blood purifying apparatus at the time of blood flowing in, the flow within the blood port at the time of blood return, and the blood return state at the perimeter, can be observed.

Next, the method for quantifying the amount of blood remaining within the blood purifying apparatus following blood return will be described.

Blood remaining within the blood ports at the blood intake side and outlet side of the blood purifying apparatus following blood return was collected, and the blood amount was measured. Following removing of the residual model blood from both blood ports, the model polymer solution was caused to flow in from the blood outlet side to the intake side, washing was continued unit outflow of residual blood from the hollow fibers could no longer be observed, this discharged fluid was collected, and the liquid amount was measured. For each solution, twice the amount of RO water was added to several ml of each so as to cause hemolysis, ultraviolet and visible light absorbancemeasurements were performed with a detecting wavelength of 414 nm, thus calculating the hemoglobin concentration with the solutions, and how much residual blood occurred in terms of conversion to model blood and the amount of residual blood per unit area of hollow fiber membrane were quantified. Measuring the amount of residual blood according to the above operations showed that the amount of residual blood per unit area of hollow fiber membrane was 1.03 ml/m².

Comparative Example 1

Blood ports were manufactured wherein the inclination θ was 2.0°, β was 10°, and wherein R, r, H, h, and D were respectively 8 mm, 2 mm, 26 mm, 2 mm; and 43.5 mm, and attached to the blood intake side and outlet side of the blood processing apparatus main unit housing filled with the hollow fibers, thus forming a blood processing apparatus otherwise the same as that in First Embodiment.

In the same manner as with First Embodiment, the above prepared bovine blood heated to 37° C. was used for perfusion in the above blood processing apparatus, and observing the blood fluid motion state macroscopically while applying light to the blood port portion after 15 minutes allowed confirmation that the flow speeds in the bending direction of the blood circuit and the direction having a 180° angle from the bending direction were faster than other directions, and that there were two stagnation areas occurring at positions approximately 30° from the bending direction of the blood circuit.

Figure 7:
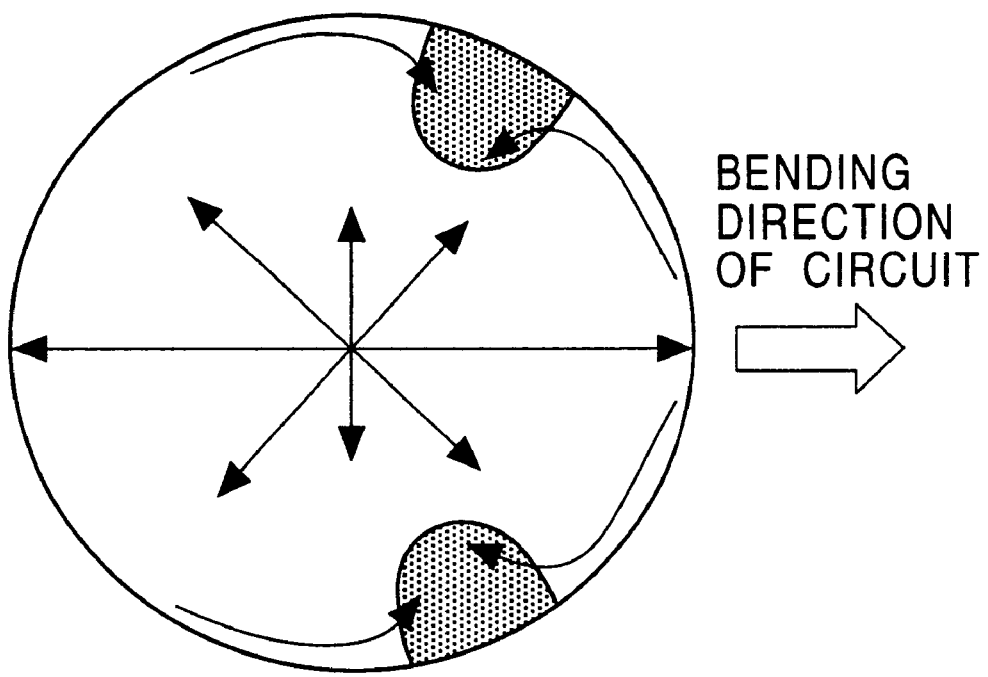
FIG. 7 is a diagram illustrating an example of blood flow within the blood port in the event that a conventional blood processing apparatus is used for blood processing.

This blood processing apparatus was used for blood dialysis for four hours, which resulted in an unequal flow as shown in FIG. 7 since the blood circuit was bent near the blood intake, causing stagnation. Regarding this area, performing the blood return operation following dialysis of four hours allowed observation of a residual blood hollow fiber band of 5 mm to 10 mm in width at the blood processing apparatus side.

The blood dialysis was performed on 11 patients 3 times each for a total of 33 times, and the residual blood state following the blood returning operation was observed in the same manner as with First Embodiment, which showed that the average residual blood score was 1.6. Incidentally, the 11 patients were the same patient group as with First Embodiment.

With the parallel perfusion test using a beagle dog, the score was 2.0 as compared to 3.5 for the BG-1.6U.

SECOND EMBODIMENT

Blood ports were manufactured wherein the minor axis/major axis ratio, db/da, of the hollow fiber flux, was 0.95, θ was 1.0°, β was 6°, and wherein R, r, H, h, and D were respectively 3 mm, 4 mm, 26 mm, 4 mm, and 41.0 mm, and attached, thus forming a blood processing apparatus otherwise the same as that in First Embodiment. Protein adhesion amounts were measured for this blood processing apparatus using bovine serum (JRS Bioseiences Bovine calf serum Cat. No.=12133-78p), which yielded 1.0 g/m². With a parallel perfusion test for the obtained module using a beagle dog, the score was 1.0 as compared to 3.5 for the BG-1.6.

The blood dialysis was performed on 11 patients 3 times each for a total of 33 times, and the residual blood state following the blood returning operation was observed in the same manner as with Third Embodiment, which showed that the average residual blood score was 1.2. Incidentally, the 11 patients were the same patient group as with First Embodiment.

Also, measuring the residual model blood amount with the same method as with First Embodiment showed that the amount of residual model blood per unit area of hollow fiber membrane was 0.56 ml/m².

Comparative Example 2

An amount of 17.9 parts by weight of syn-PMMA having molecular weight of 400,000 by weight average according to polystyrene conversion GPC method and 45.5 parts by weight of syn-PMMA having molecular weight of 1,400,000 by weight average, 17 parts by weight of iso-PMMA having molecular weight of 600,000 by weight average, 20 parts by weight of co-PMMA, and 376 parts by weight of dimethyl sulfoxide were mixed and stirred for 8 hours at 110° C., thereby obtaining a spinning fluid. The viscosity of the obtained spinning fluid was 2,600 poise. The obtained spinning fluid was discharged from a ring slit type hollow nozzle with an outer diameter/inner diameter of 2.1/1.95 mm diameter that was maintained at 96° C., at a rate of 1.1 g/min, into the atmosphere. At the same time, nitrogen gas was injected into the hollow interior. The length of the dry portion was 50 mm, and water of 40° C. was used for the coagulation bath. The inner diameter/membrane thickness of the hollow fiber was 200/30 μm.

The surface coarseness average value per 0.1 mm reference length of ten of the obtained hollow fibers was 0.52 μm.

The hollow fibers were cut. into 22 cm length, 15,768 of such fibers were bundled, placed in housing formed of a polystyrene tube with a 35 mm diameter having a intake opening and outlet opening for blood processing fluid, both ends thereof were fixed with resin, then cut with a steel blade at a tip angle of 68°. The surface coarseness of the blood intake portion (maximum height) at this time was 14 μm per 0.1 mm reference length at the blood intake portion. Also, the minor axis/major axis ratio, db/da, of the hollow fiber flux, was 0.90.

Blood ports wherein θ was 2.0°, β was 10°, and R, r, H, h, and D were respectively 8 mm, 2 mm, 26 mm, 2 mm, and 43.5 mm, were attached thereto, thus forming a blood processing apparatus with a valid membrane length of 19 cm, and valid membrane area of 1.6 m². The inner surface coarseness per 0.1 mm reference length for this blood port was 0.3 μm, and D−da was 2.5 mm. Also, permeability thereof was 80 ml/hr·mmHg. Protein adhesion amounts were measured for this blood processing apparatus using bovine serum (JRS Bioseiences Bovine calf serum Cat. No.=12133-78p), which yielded 1.4 g/m².

With a blood perfusion experiment using a beagle dog as performed with First Embodiment, the average residual blood score was 3.5, the same as BG1.6U.

Also, measuring the residual model blood amount with the same method as with First Embodiment showed that the amount of residual model blood per unit area of hollow fiber membrane was 1.69 ml/m².

Comparative Example 3

The hollow fibers in First Embodiment were cut into 22 cm length, 15,768 of such fibers were bundled, placed in housing formed of a polystyrene tube with a 35 mm diameter having a intake opening and outlet opening for blood processing fluid, both ends thereof were fixed with resin, then cut with a steel blade at a tip angle of 68°, thus forming a blood processing apparatus otherwise the same as that in Comparative Example 1. The surface coarseness was 14 μm per 0.1 mm reference length at the blood intake portion. With a blood perfusion test using a beagle dog as performed with First Embodiment, the average residual blood score was 2.5 as compared to 3.5 for the BG1.6U, which was worse than Comparative Example 1, due to the great roughness at the edge plane.

THIRD EMBODIMENT

A blood processing apparatus was formed the same as that in Second Embodiment, except that the hollow fiber membrane from Comparative Example 2 was used. With a blood perfusion experiment using a beagle dog as with First Embodiment, the average residual blood score was 1.8 as compared to 3.5 for the BG1.6U.

FOURTH EMBODIMENT

A blood processing apparatus was formed the same as that in First Embodiment, except that the inner surface coarseness of the blood port was 0.8 μm per 0.1 mm reference length. With a blood perfusion experiment using a beagle dog, the average residual blood score was 1.5 as compared to 3.5 for the BG1.6U, though no white sediments owing to fibrin was observed on the inner surface of the blood port.

Comparative Example 4

A blood processing apparatus was formed the same as that in Comparative Example 2, except that the inner coarseness of the blood port was 1.3 μm per 0.1 mm reference length. With a blood perfusion experiment using a beagle dog, white sedimentation owing to fibrin was observed on the inner surface of the blood port. The average residual blood score was 3.5 as compared to 3.5 for the BG1.6U.

FIFTH EMBODIMENT

The blood processing apparatus according to Comparative Example 2 was subjected to 20 minutes of perfusion with a 500 ppm polyethylene glycol (#6000) aqueous solution under a flow amount of 500 ml/min, thus forming a blood processing apparatus with adhesion of polyethylene glycol. The surface roughness within the hollow fibers and the roughness at the edge planes were the same as with First Embodiment. With a parallel perfusion experiment using a beagle dog as with the method in First Embodiment, the average residual blood score was 0.5 as compared to 3.5 for the BG1.6U.

SIXTH EMBODIMENT

An amount of 180 g of polysulfone, 90 g of polyvinyl pyrolidone (K-30), and 1 g of water were added to 729 g of DMAC and heated and dissolved for 8 hours at 80° C., thereby obtaining a spinning fluid. The dissolved fluid was allowed to stand for 10 hours to defoam. A mixed fluid of DMAC 60% and water was used for the injecting fluid. The prepared fluid and injecting fluid were discharged from a double slit nozzle with an outer diameter/inner diameter of 0.28/0.20 mm diameter that was maintained at 30° C, the injecting fluid from the inside and the spinning fluid from the outside, and coagulated in a hollow fiber form in a coagulation bath of 59° water. The hollow fiber was wound at a winding speed of 32.2 m/min, thus obtaining a sample. The inner diameter of the hollow fiber 200 μm,, and the membrane thickness 40 μm. Permeability of the hollow fiber was 1110 mmHg/hr/m².

The surface coarseness per 0.1 mm reference length of ten of the obtained hollow fibers was measured, showing that the average value thereof was 0.07 μm. The hollow fibers were cut into 24 cm length, 10,600 of such fibers were bundled, placed in housing formed of a polystyrene tube with a 35 mm diameter having a intake opening and outlet opening for blood processing fluid, both ends thereof were fixed with resin, then cut with a steel blade at a tip angle of 30°, thus forming a smooth plane. The surface roughness of the blood intake portion at this time was 6 μm. The minor axis/major axis ratio, db/da, of the hollow fiber flux, was 0.95.

Blood ports wherein θ was 1.0°, β was 6°, and R, r, H, h, and D were respectively 3 mm, 4 mm, 26 mm, 4 mm, and 41.0 mm, were attached thereto, thus forming a blood processing apparatus with a valid length of 19 cm, and valid membrane area of 1.3 m². With a parallel perfusion experiment for this blood processing apparatus using a beagle dog as performed with Second Embodiment, the average residual blood score was 1.0, as compared to 3.0 for the BG1.6U.

Comparative Example 5

A blood processing apparatus was formed the same as that in Second Embodiment, except that the ratio of hollow fibers having a minor axis 70% or shorter than the value of minor axis=major axis was 30% of the entirety of the blood purifier. Performing residual blood amount quantifying experimentation in a model system with the same method as with First Embodiment showed that the amount per unit area of hollow fiber membrane was 8.13 ml/m².

Comparative Example 6

A blood processing apparatus was formed using cellulose triacetate hollow fibers, and with a blood purifier satisfying the conditions of db/da=0.95 with the major axis of the envelope of the hollow fiber flux as da and the minor axis of the envelope of the hollow fiber flux as db, C value=3.0 mm, opening ratio=28%, θ=9°, and h=4 mm, measuring the residual model blood amount with the same method as with First Embodiment showed that the amount of residual model blood per unit area of hollow fiber membrane was 1.52 ml/m².

INDUSTRIAL APPLICABILITY

Thus, according to the present invention, a blood processing apparatus with little residual blood can be provided, and can be suitably used for blood purifying, dialysis, ultrafiltration, and the like.

What is claimed is:

1. A blood processing apparatus having a hollow fiber bundle fixed to a housing by a partition with an end portion of the hollow fiber bundle opened, and a blood port provided with a blood intake attached to said end portion, the blood intake having an interior wall and an exterior wall; wherein an angle of the blood intake interior wall provided to said blood port has an inclination $\theta$ of 1.5° or less as to a center axis of said blood port, and the expression $0.08 \, D \leq h \leq 0.13 \, D$ holds, wherein an inner surface of the blood port has a smooth surface or has an inner plane coarseness of up to 0.3 $\mu$m per 0.1 mm reference length, and Q represents the intersection between a hypothetical line which passes through the end portion P of the inner plane of said blood port and is orthogonal with said partition and a hypothetical extension line from the ceiling plane of said blood port, h represents the distance between said partition and said intersection Q, and D represents the diameter at the end portion of the inner plane of said blood port.

2. A blood processing apparatus according to claim 1, wherein an inner portion of the blood port facing the open end plane of the partition is an angle $\beta$ formed between the hypothetical extension line from the ceiling plane of said blood port and said partition is $4° \leq \beta \leq 10°$.

3. A blood processing apparatus according to claim 1, wherein $db/da \geq 0.95$ and/or $D-da \leq 2$ mm hold wherein da represents the major axis of the hollow fiber flux at the opening end portion of said hollow fiber flux and db represents the minor axis thereof.

4. A blood processing apparatus according to claim 1, wherein the fibers of the hollow fiber bundle are smooth or have an inner plane coarseness of up to 0.5 $\mu$m per 0.1 mm reference length.

5. A blood processing apparatus according to claim 1, wherein a face of the partition contacting the blood has a roughness of 10 $\mu$m per 30 $\mu$m reference length or less.

6. A blood processing apparatus according to claim 1, wherein the ratio of hollow fibers having a minor axis 70% or shorter than the diameter thereof in the event that the cross-section of said hollow fibers is assumed to be a perfect circle is 1% or less of the entire number of hollow fibers built into the blood purifier.

7. A blood processing apparatus according to claim 1, wherein said hollow fibers comprise polymers that have been made to be hydrophilic as a component.

* * * * *